United States Patent [19]
Fox et al.

[11] Patent Number: 6,050,989
[45] Date of Patent: Apr. 18, 2000

[54] ANGULARLY ADJUSTABLE POWERED SURGICAL HANDPIECE

[75] Inventors: Brian J. Fox; Thanh Trong Tran, both of St. Petersburg; Kenneth M. Adams, Tampa, all of Fla.

[73] Assignee: Linvatec Corporation, Largo, Fla.

[21] Appl. No.: 09/138,938

[22] Filed: Aug. 24, 1998

[51] Int. Cl.⁷ .................................................. A61B 17/00
[52] U.S. Cl. ............................ 606/1; 285/184; 433/130; 433/133; 81/57.26
[58] Field of Search ................................ 606/1; 173/216, 173/217; 81/57.26, 177.7, 177.8, 177.9; 403/99, 101, 102, 103; 285/184; 433/130, 133; 464/106

[56] References Cited

U.S. PATENT DOCUMENTS

| | | |
|---|---|---|
| 636,476 | 11/1899 | Webster . |
| 1,160,213 | 11/1915 | Tappan . |
| 1,677,337 | 7/1928 | Grove . |
| 2,286,498 | 6/1942 | Miller, Jr. . |
| 2,316,243 | 4/1943 | Hubbard . |
| 2,584,097 | 1/1952 | Trbojevich . |
| 3,509,629 | 5/1970 | Kidokoro et al. ........................ 433/114 |
| 3,847,154 | 11/1974 | Nordin ..................................... 606/180 |
| 4,071,029 | 1/1978 | Richmond et al. ...................... 606/180 |
| 4,347,450 | 8/1982 | Colligan ..................................... 310/50 |
| 4,449,956 | 5/1984 | Ueno . |
| 4,748,872 | 6/1988 | Brown .................................... 81/57.26 |
| 4,947,942 | 8/1990 | Lightle et al. . |
| 5,073,145 | 12/1991 | Ratzokwski et al. . |
| 5,352,234 | 10/1994 | Scott ...................................... 606/170 |
| 5,372,420 | 12/1994 | Van Deursen et al. .................. 366/129 |
| 5,549,634 | 8/1996 | Scott et al. .............................. 606/170 |
| 5,569,090 | 10/1996 | Hoskins et al. . |
| 5,569,256 | 10/1996 | Vaughn et al. ............................. 606/80 |

*Primary Examiner*—Linda C. M. Dvorak
*Assistant Examiner*—Brad C. Blaise
*Attorney, Agent, or Firm*—Gene Warzecha

[57] ABSTRACT

An adjustable collet mechanism for a surgical handpiece which enables the surgical tool driven by the handpiece to be oriented at selected angular positions relative to the handpiece axis. The coupling means includes a non-rotatable sleeve attached to the handpiece and a rotatable sleeve attached to the collet holding the surgical tool. The abutting faces of the non-rotatable and rotatable sleeves are angled relative to the handpiece axis so that relative rotation of the components causes their axes to be positionable either in alignment or at a predetermined angular orientation. The coupling mechanism includes a tubular coupling link which enables relative rotation between the rotatable and non-rotatable sleeves while also enabling translation of power from the handpiece to the surgical tool.

14 Claims, 15 Drawing Sheets

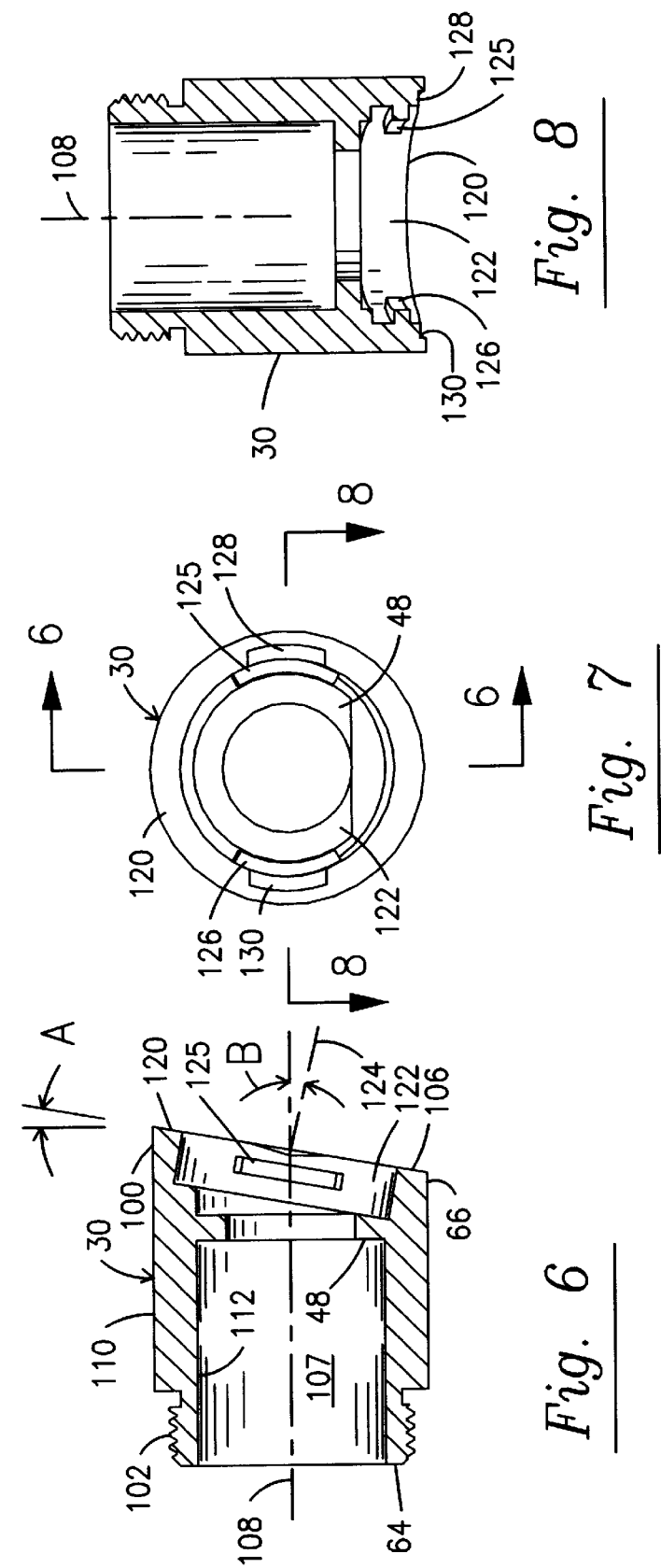

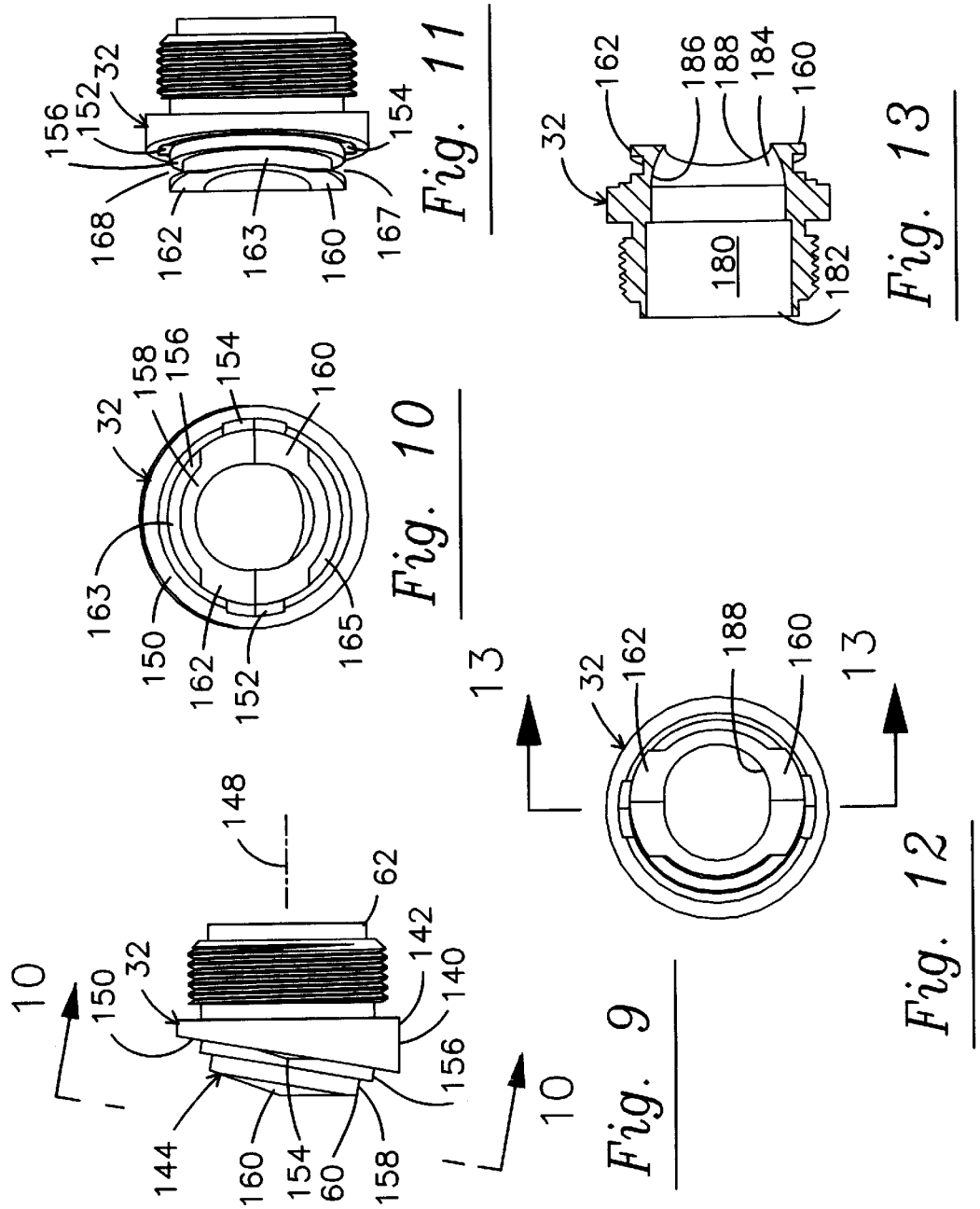

ANGULARLY ADJUSTABLE POWERED SURGICAL HANDPIECE

BACKGROUND OF THE INVENTION

1. Field of the Invention

The invention relates to powered surgical instruments. In particular, the invention relates to a handpiece to which a variety of surgical tools may be attached. Still more particularly, the invention relates to the method and apparatus by which the collet mechanism holding the tool may be attached to the handpiece and selectively adjustable, i.e. bendable, to one of a plurality of positions relative to the handpiece body.

2. Description of the Prior Art

Surgical handpieces for driving a variety of surgical tools are well known for both open and closed surgical procedures (i.e. endoscopic, arthroscopic, etc.). Such instruments generally comprise a powered handpiece having a distal end to which a variety of surgical tools may be attached by means of some chuck or collet mechanism. The handpiece receives power at its proximal end from any one of a number of sources (e.g. pneumatic, electric, battery) and contains a drive means for providing rotary (or other) power to the surgical tool. It is known to provide attachments for the distal tips of handpieces by which the various tools may be oriented at selected positions relative to the handpiece body. Generally, the axis of the tool is able to be placed by a user either in a position coaxial to the drive axis of the handpiece body, i.e. a straight orientation, or one or more other positions in which the tool axis intersects with but is angled relative to the drive axis of the handpiece body, i.e. an angled orientation. It will be understood that the term "drive axis" means the main axis along which power is transmitted (e.g. a rotating drive shaft), and as such handpieces having all configurations (pencil-type, pistol grip, etc.) will have such a drive axis.

Such adjustability of tool orientations is usually provided by fixed attachments interposed between the collet mechanism and the handpiece. For example, the Hall Ultrapower® Drill System manufactured by Linvatec Corporation, Largo, Fla. 33773 provides a variety of burr guards in various lengths and fixed angular orientations in order to enable a user to choose between using the tool in coaxial alignment with the handpiece or in a fixed angular orientation relative to the handpiece. However, because of the fixed nature of the angled burr guards, a user must have available both straight and angled attachments in order to have the flexibility of choosing a particular orientation at the time of surgery. It would be preferable, and it is an object of this invention, to enable the user to minimize the number of attachments that must be held in inventory while still enabling the user to select a particular tool orientation at the time of surgery.

It is also known to provide adjustability of tool orientation by a variable attachment interposed between the collet mechanism and the handpiece. One such device is shown in U.S. Pat. No. 636,476 (Webster) as embodied in a dental handpiece having the drill adjustable into a variety of positions relative to the handpiece body. The chuck mechanism in this device must be locked into a selected position by placing a retaining pin in corresponding apertures.

It is an object of this invention to produce a bendable collet mechanism for a powered surgical handpiece so that a surgical tool may be selectively placed into one of a plurality of positions relative to the handpiece body and automatically held in the selected position during use.

It is another object of this invention to provide such an adjustable collet mechanism which is usable without the necessity for other tools to lock or unlock the collet mechanism from any of its possible positions relative to the handpiece body.

It is also an object of this invention to provide a system for enabling a user to selectively choose between straight and angled tool orientations.

SUMMARY OF THE INVENTION

These and other objects of the invention are achieved by the preferred embodiment disclosed herein which is an adjustable collet mechanism for a surgical handpiece which enables the surgical tool driven by the handpiece to be oriented at selected angular positions relative to the handpiece axis. The coupling means includes a non-rotatable sleeve attached to the handpiece and a rotatable sleeve attached to the collet holding the surgical tool. The sleeves have abutting inclined faces which are angled relative to the handpiece axis so that relative rotation of the components causes their axes to be positionable either in alignment or at a predetermined angular orientation. The coupling mechanism includes a tubular coupling link to enclose a drive train to power the tool, thus enabling relative rotation between the rotatable and non-rotatable sleeves while also enabling translation of power from the handpiece to the surgical tool.

BRIEF DESCRIPTION OF THE DRAWINGS

FIG. 6 is a side elevational view in cross-section of the non-rotatable sleeve component of the adjustment mechanism of FIG. 1.

FIG. 7 is a front elevational view of the component shown in FIG. 6.

FIG. 8 is a cross-sectional view of FIG. 7 taken along the line 8—8.

FIG. 9 is a side elevational view of the rotatable indexing sleeve of the adjustment mechanism of FIG. 1.

FIG. 10 is an elevational view of the component shown in FIG. 9 taken along the line 10—10.

FIG. 11 is a top plan view of FIG. 9.

FIG. 12 is a right side elevational view of FIG. 11.

FIG. 13 is a cross-sectional view of FIG. 12 taken along the line 13—13.

DESCRIPTION OF THE PREFERRED EMBODIMENT

Figure 1:
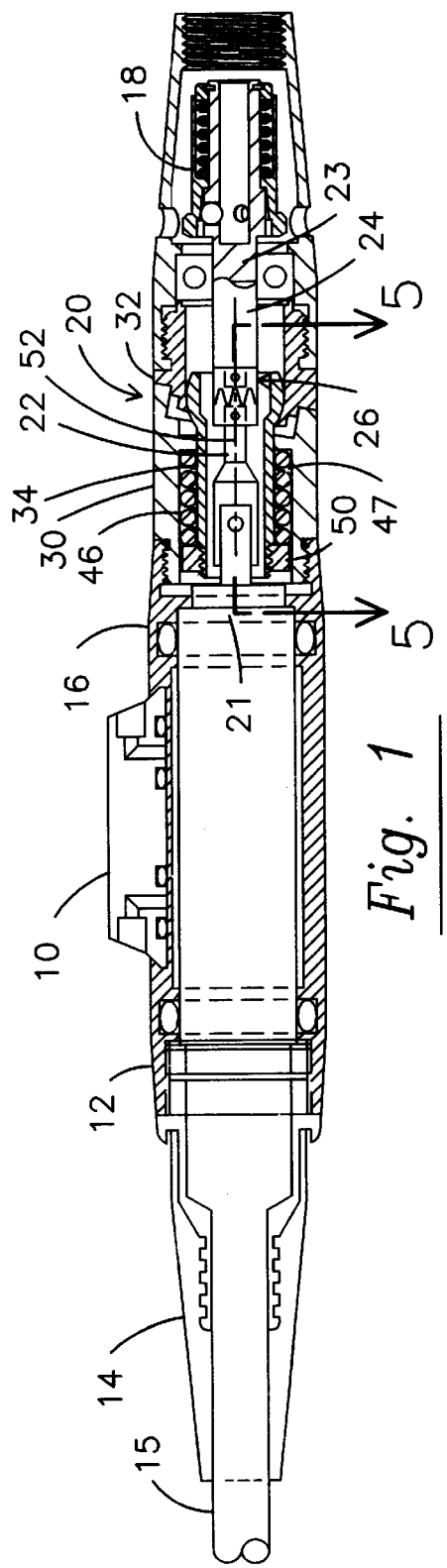
FIG. 1 is a side elevational view partially in cross-section of a handpiece provided with an adjustment mechanism constructed in accordance with the principles of this invention.
Figure 2:
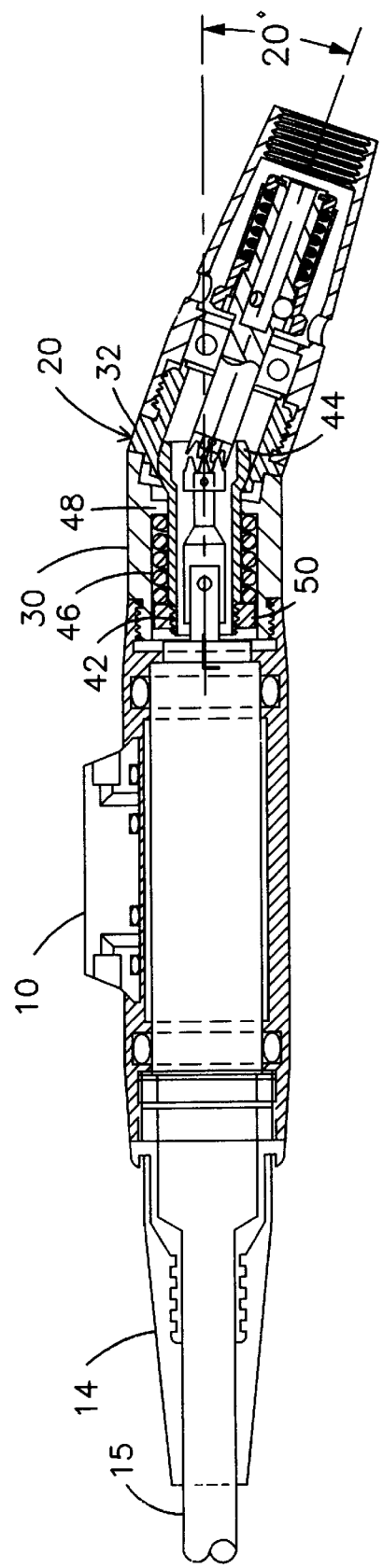
FIG. 2 is a view of FIG. 1 showing the handpiece in an angled orientation.
Figure 3:
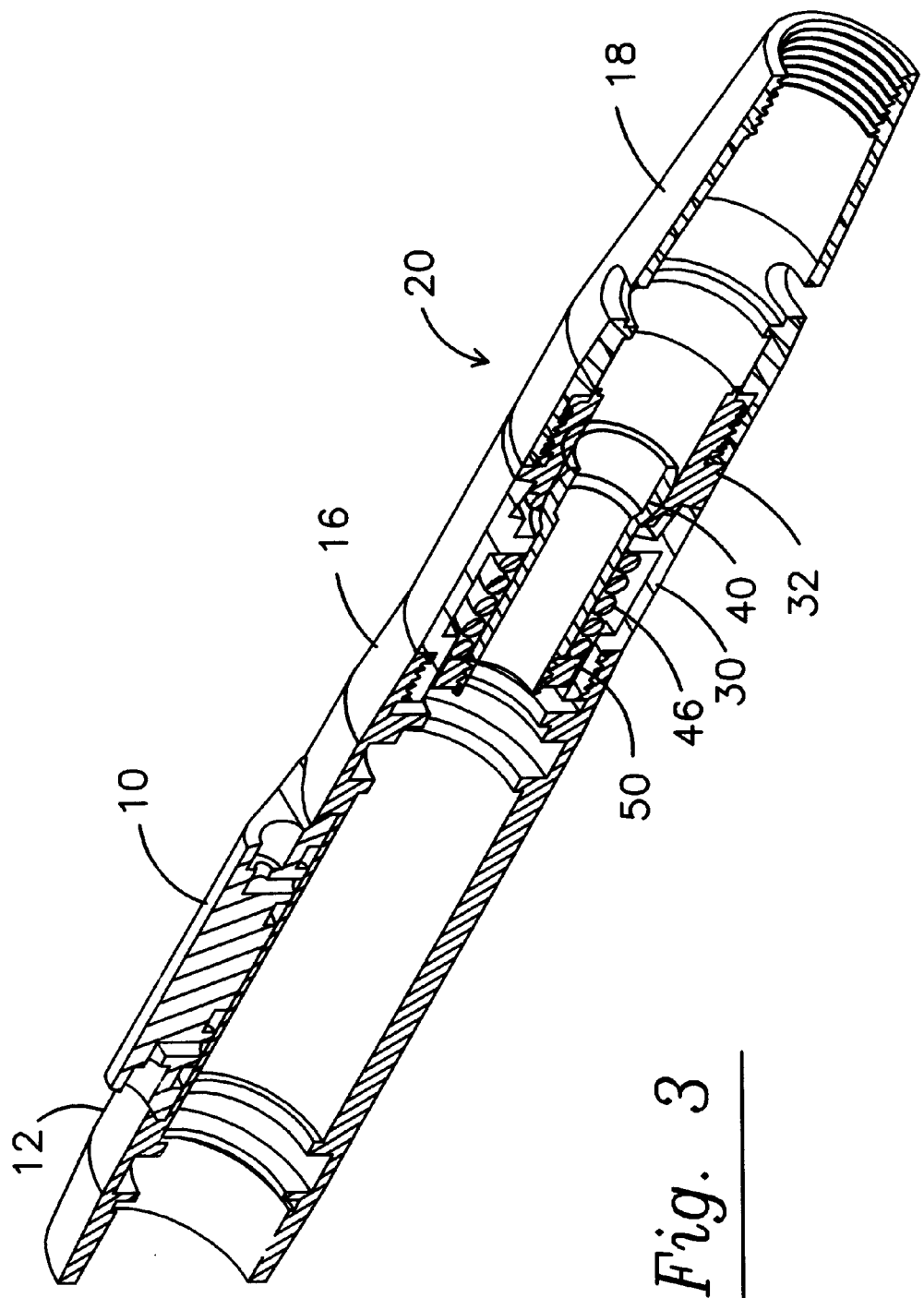
FIG. 3 is a front perspective view of the handpiece of FIG. 1 in cross-section with various internal components removed for clarity.

A powered surgical handpiece including an adjustable (bendable) collet mechanism constructed in accordance with the principles of this invention is shown in FIGS. 1 and 2. Handpiece 10 may be any one of a variety of surgical handpieces but, for the purposes of explaining the subject invention, handpiece 10 is shown in the form of an electrically powered, pencil type handpiece. It will be understood that the subject invention may be used with any number of other handpiece types.

Handpiece 10 includes a proximal end 12 attached to a cable restraining release 14 and an electrical cable 15. Obviously, the handpiece may be driven by other than electrical means. Handpiece 10 also includes a distal end 16 to which is secured a conventional tool holder such as collet mechanism 18 via an intermediate, variable orientation coupling 20. It will be understood that handpiece 10 and collet mechanism 18 may be conventional and do not form any part of the subject invention. Handpiece 10 has a drive axis 21 adjacent its distal end 16. Since the handpiece may have a variety of configurations, it will be understood that only the axis near the distal end will be referred to in describing the invention. Similarly, collet mechanism 18 has an axis 23 near its proximal end. Power is transmitted from handpiece 10 to the collet mechanism 18 via an elongated drive train comprising intermediate drive shafts 22 and 24 aligned along axes 21 and 23, respectively, and joined by, for example, a mating crown gear assembly 26 which enables the transmission of rotational motion from shaft 22 to shaft 24 as the latter is placed in various angular positions as will be understood below. Other mating drive couplings may also be used such as constant velocity universal joints.

Coupling section 20 surrounds the drive train and comprises a proximal stationary, non-rotatable cylindrical sleeve 30 having axis 21, a distal rotatable, indexing cylindrical sleeve 32 having axis 23 and a hollow tubular or cylindrical coupling body 34. In the preferred embodiment, sleeve 30 is threadably or otherwise fixedly joined at its proximal end to the distal end 16 of the handpiece and rotatable indexing sleeve 32 is threadably or otherwise fixedly joined at its distal end to the proximal end of the collet mechanism 18. The sleeves 30 and 32 are movable relative to each other, but fixed relative to the handpiece and collet, respectively.

While sleeve 32 is described as being rotatable relative to sleeve 30, it will be understood below that the motion of sleeve 32 is more in the nature of a nutation. That is, axis 23 nutates about axis 21 as sleeve 32 is turned.

Sleeve 30 and indexing sleeve 32 are held in abutting relationship by spring-loaded tubular coupling body 34 which has a threaded proximal end 42 and a partially spherical distal end 44. As shown in the configuration of FIG. 1, axis 52 of the coupling body 34 is coaxially aligned with handpiece axis 21 and with axis 23 of shaft 24. A coil spring 46 is interposed between the inner tubular or cylindrical surface of the sleeve 30 and the outer surface of coupling body 34 in an annular space 47 and is retained in place between radially inwardly extending annular flange 48 and nut 50 threaded onto the proximal end 42 of the cylindrical body. Radially inwardly extending annular flange 48 has an axially aligned opening sized and shaped to receive the outer surface of body 34 which, in the preferred embodiment, is cylindrical. The outer diameter of nut 50 is sized and shaped to be slidably received within the interior of sleeve 30. The body 34 is thus maintained in coaxial alignment with the axis 21 of the handpiece and biased in a proximal direction to urge sleeves 30 and 32 together as will be understood below.

Figure 4:
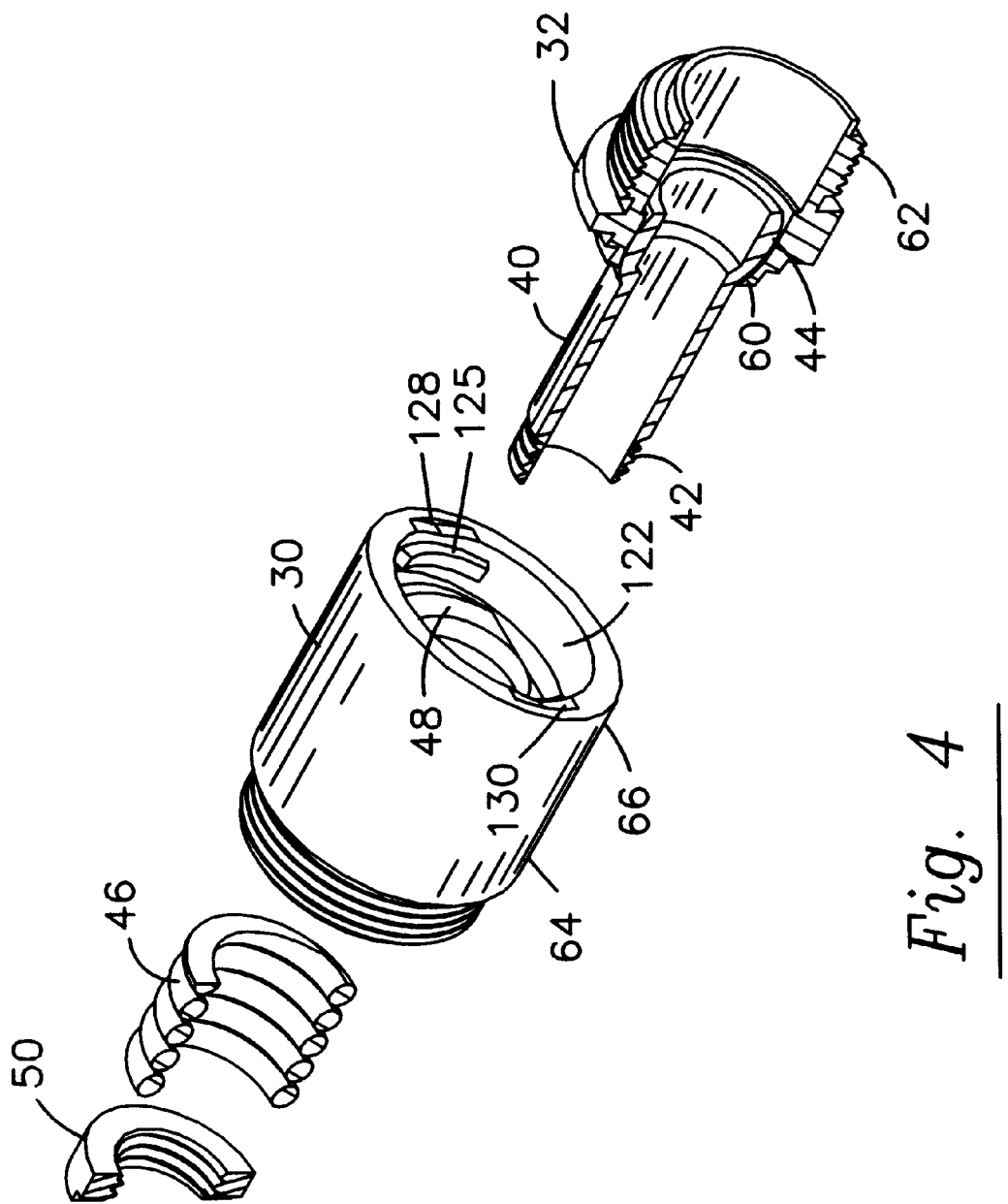
FIG. 4 is an expanded front perspective view of the adjustment mechanism, partially in cross-section.
Figure 5:
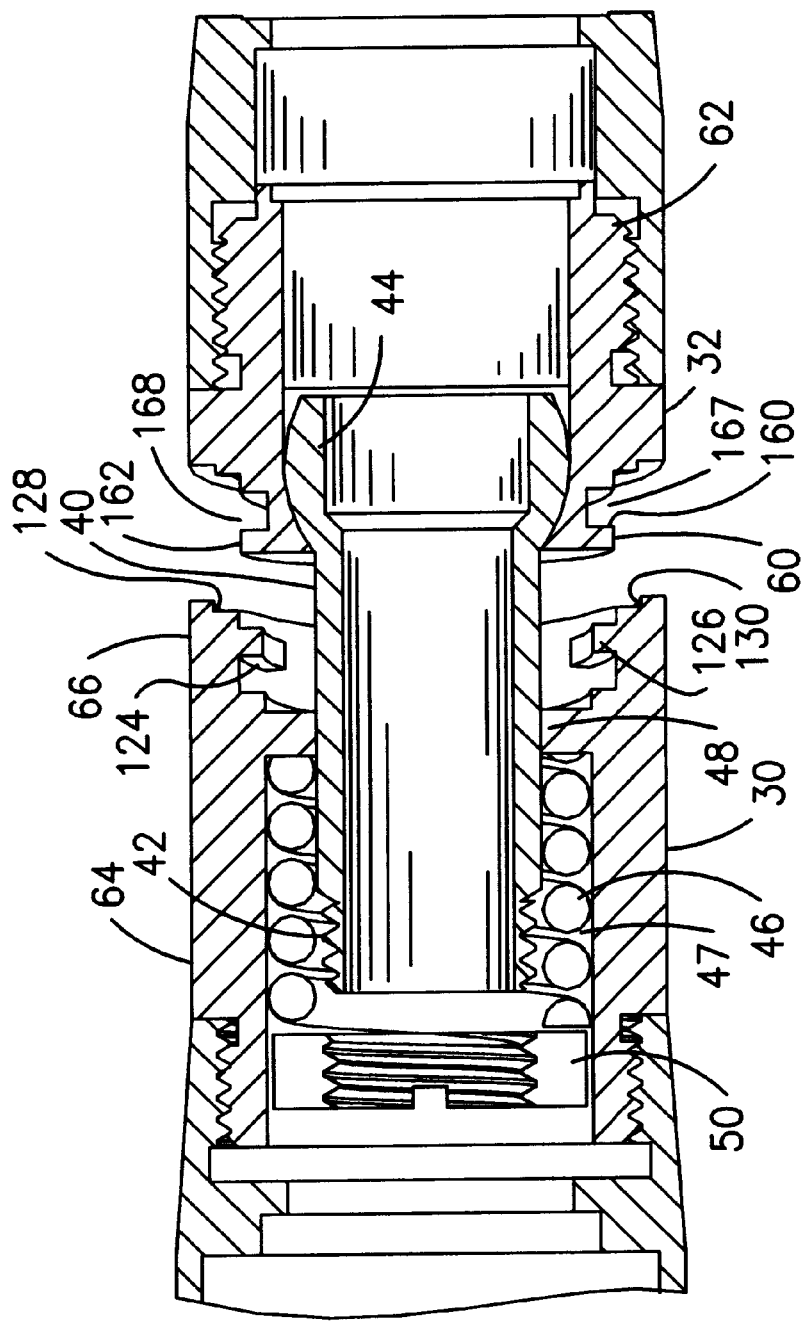
FIG. 5 is a partially expanded cross-sectional view of the adjustment mechanism taken along the line 5—5 of FIG. 1, omitting some components for clarity.

As best seen in FIGS. 4 and 5, with the components separated for clarity, rotatable indexing sleeve 32 has proximal and distal ends 60 and 62, respectively, and non-rotatable sleeve 30 has proximal and distal ends 64 and 66, respectively. As will be explained below, the distal end 66 of non-rotatable sleeve 30 and the proximal end 60 of sleeve 32 have mutually complementarily shaped features enabling these ends to be held together in either coaxial alignment as shown in FIG. 1 or at some predetermined angle which in the preferred embodiment is approximately 20°, as shown in FIG. 2.

The detailed structures of stationary sleeve 30 and rotatable indexing sleeve 32 are best seen by reference to FIGS. 6 through 13. Stationary sleeve 30 is a tubular body 100 having a thread 102 at its proximal end 64, an inclined distal surface 106 at its distal end 66 and a main axis 108. The exterior surface 110 of body 100 may be shaped so as to blend with and serve as part of the exterior surface of the handpiece as best seen in FIGS. 1 and 2. In the preferred embodiment, surface 110 is cylindrical. The interior surface 112, which may also be cylindrical, defines a chamber 107 for retaining spring 46, nut 50 and coupling body 40 (as best seen in FIGS. 1, 2 and 5). Chamber 107 is sufficiently large to receive all these components and is bounded at its distal end by annular flange 48. Distal surface 106 has an annular face 120 which lies in a plane angled at an angle A relative to a plane perpendicular to axis 108. The distal end 106 also defines a cylindrical chamber 122 having an axis 124 inclined relative to axis 108 at an angle B. Chamber 122 includes a pair of diametrically opposed, radially inwardly extending tabs 125 and 126 having a predetermined arcuate length and situated within a plane parallel to that of face 120 and spaced proximally therefrom by a predetermined distance. Tabs 125 and 126 are arcuate by virtue of the fact that they follow the contour of the inside cylindrical surface of chamber 122. Adjacent each tab 125 and 126, face 120 is provided with a diametrically opposed pair of shallow detents 128 and 130 which, as best seen in FIGS. 4 and 6, each take the form of arcuate shallow triangular recess having a large opening on face 120 and an apex spaced proximally therefrom.

Indexing sleeve 32 comprises a tubular body 140 having an exterior surface 142, a proximal end 60, a distal end 62 and an axis 148. Exterior surface 142 has a shape comparable to that of the exterior surface of stationary sleeve 30 and serves as a portion of the exterior surface of the handpiece as best seen in FIGS. 1 and 2. In the preferred embodiment, exterior surface 142 is cylindrical and has a diameter equal to that of exterior surfaces of body 100 (FIG. 6) and collet 18 (FIG. 1). Proximal end 60 is provided with locking features 144 intended to complementarily mate with the distal end 66 of sleeve 30 and to provide a selectively lockable engagement therewith. Proximal end 60 is also provided with an annular face 150 intended to be placed in abutting relationship with face 120 of the stationary sleeve. Face 150 is provided with a pair of diametrically opposed projections 152 and 154 intended to be matingly received within detents such as triangular recesses 128 and 130. As will be understood below, the recesses and projections may be alternatingly engaged depending upon the angular orientation of sleeve 32 relative to sleeve 30. That is, recess/projection pairings could be, for example, 128/154 and 130/152 if the tool is positioned in alignment with the handpiece axis, or 128/152 and 130/154 if the tool is angled. A raised spacing cylinder 156 extends distally from face 150 and a second spacing cylinder 158 extends distally from cylinder 156. The distal end of cylinder 158 is provided with a pair of diametrically opposed tabs 160 and 162. As best seen in FIGS. 5, 10 and 11, tabs 160 and 162 have an outer arcuate surface having a diameter equal to that of spacing cylinder 156 thereby producing arcuate gaps 163 and 165 between tabs 160 and 162 and spacing cylinder 156 as seen in FIG. 11. This results in arcuate spaces 167 and 168 behind tabs 160 and 162, respectively.

The interior 180 of indexing sleeve 32, best seen in FIG. 13, has a distal end 182 and a proximal end 184 which is provided with spherical wall surface 186. An aperture 188 at the proximal end is sized to receive the cylindrical portion of coupling body 40 so that wall surface 186 may engage the spherical distal end 44 of the coupling body. Aperture 188 is smaller than the diameter of the spherical surfaces in order to maintain longitudinal tension on the spherical surfaces to keep the components together. Thus, sleeve 32 is able to nutate about sleeve 30 while faces 120 and 150 remain in contact.

Figure 14:
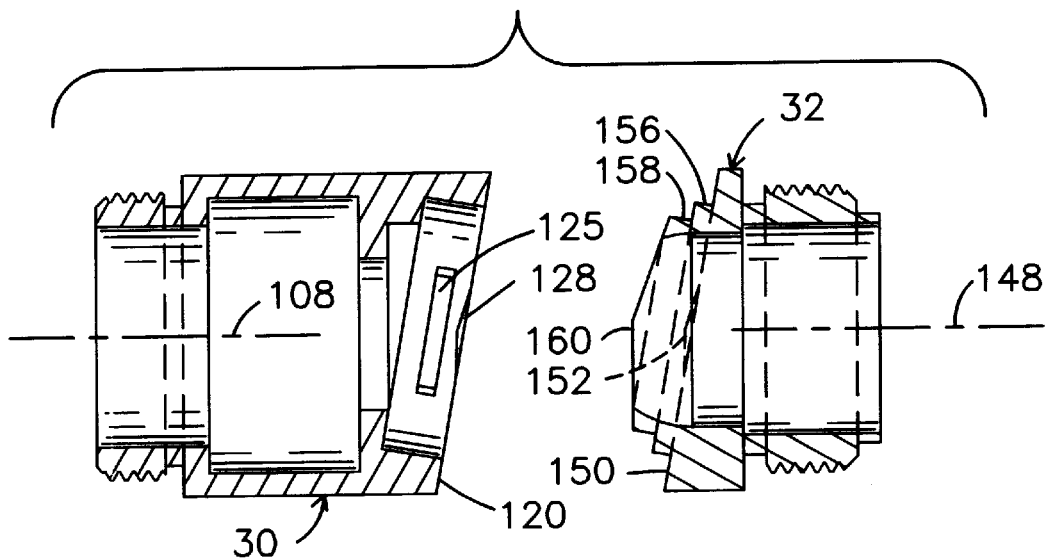
FIGS. 14 and 15 are expanded and assembled side elevation views in cross-section, respectively, of the rotatable and non-rotatable sleeves of the adjustment mechanism showing the configuration of the components in a straight orientation.
Figure 15:
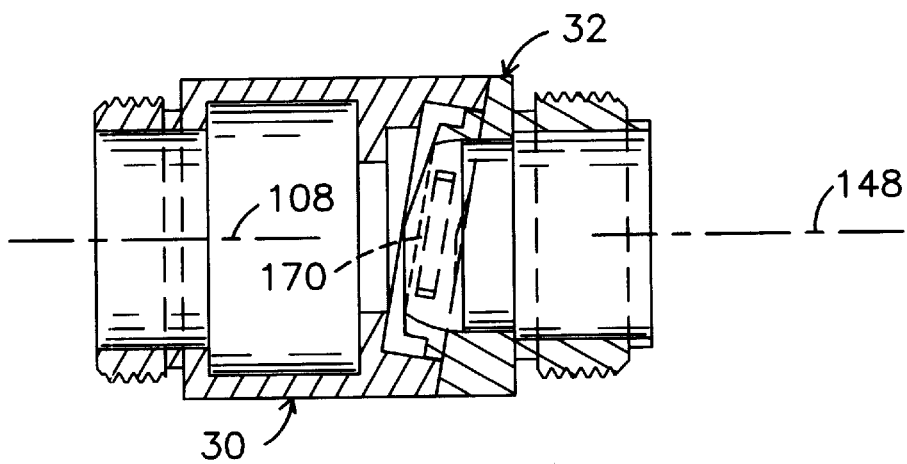
Figure 16:
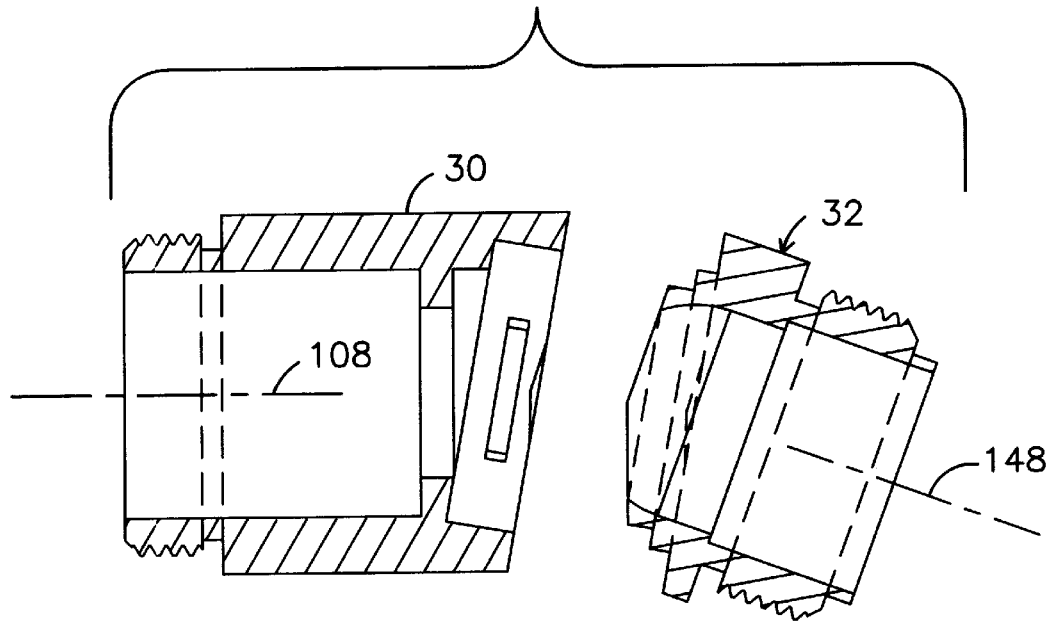
FIGS. 16 and 17 are expanded and assembled views, respectively, of the components of FIGS. 14 and 15 showing the components in an angled orientation.
Figure 17:
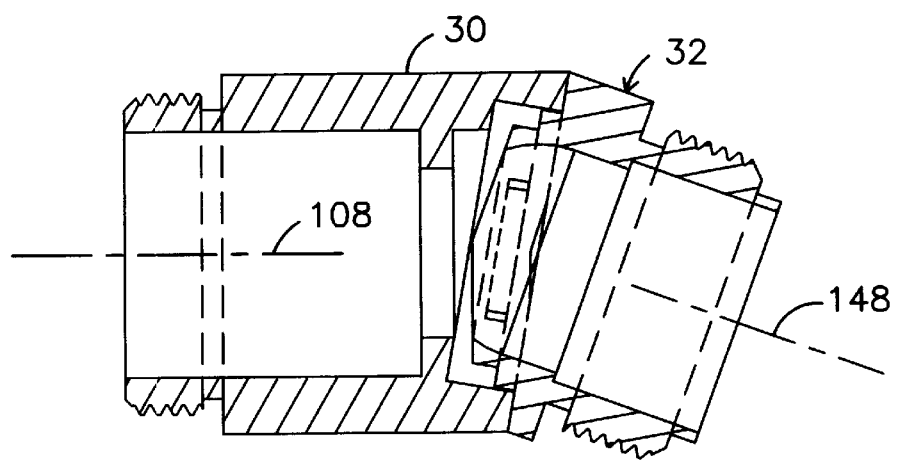

The operation of the bendable collet mechanism is best understood by reference to FIGS. 14 through 17 which show stationary sleeve 30 and rotatable indexing sleeve 32 with their axes 108 and 148 coaxially aligned (FIG. 14 and 15) and with their axes angularly oriented (FIG. 16 and 17). Coupling body 34 and other components have been omitted from these drawings for clarity. As shown in these drawings, when the sleeves are aligned such that tabs 160, 162 are horizontally oriented the same way as tabs 124, 126, the tabs interfere and prevent the sleeves from engaging. When sleeve 32 is rotated about is axis 148 by 90° from the position shown in FIG. 14 (or that shown in FIGS. 15–17), the tabs 160, 162 will be oriented along a line situated 90° relative to a line through tabs 124, 126 and the sleeves may then be engaged and rotated again by 90° relative to each other such that coaxially arcuate tab 160 will be received proximally of arcuate tab 124 on sleeve 30, as shown in FIG. 14. It will be understood that the opposite tabs are similarly engaged, but omitted for clarity. When the sleeves are so engaged and urged together by spring tension, a small gap 170 may exist between tab 124 and tab 160 when surfaces 120 and 150 are in abutting engagement. It will be understood that spring 46 will urge coupling body 34 proximally so that the spherical distal end 44 may urge the partially enclosed proximal end 184 of sleeve 32 in a proximal direction in order to maintain contact between surfaces 120 and 150. Some gap 170 is necessary if projections 152, 154 and their corresponding recesses 124, 126 are utilized. That is, since rotation of sleeve 32 relative to sleeve 30 is necessary in order to reposition sleeve 32 from the straight orientation of FIGS. 14 and 15 to the angular orientation shown in FIGS. 16 and 17, the projections are necessarily pushed from their corresponding recesses as one sleeve rotates relative to the other. This necessarily causes surface 120 to be spaced from surface 150 by the height of the projection and minimizes gap 170 by moving tabs 160, 162 distally, that is, longitudinally closer to tabs 124, 126 as the two sleeves rotate relative to each other. Thus, in this embodiment, since the strength of spring 46 defines the degree of force with which the two sleeves are urged together, a laterally directed force on the tool to be attached to collet mechanism 18 may result in a laterally directed force on sleeve 32 which may cause some slight angular movement of the axis of sleeve 32 until the tabs 160, 162 actually touch the proximally facing surfaces of tabs 124, and 126. Minimizing the size of this gap and increasing the strength of spring 46 will tend of minimize the degree of such movement.

Referring now to FIGS. 18–26, there is shown an alternate embodiment of the bendable collet mechanism constructed in accordance with the principles of this invention. This alternate embodiment minimizes the degree to which lateral forces on the tool can cause angular misalignment of the components of the coupling. Thus, handpiece 10 and collet 18 may be joined by coupling mechanism 200 instead of coupling mechanism 20. For clarity, all of the internal components associated with actually driving the surgical tool have been omitted from these drawings.

Figure 18:
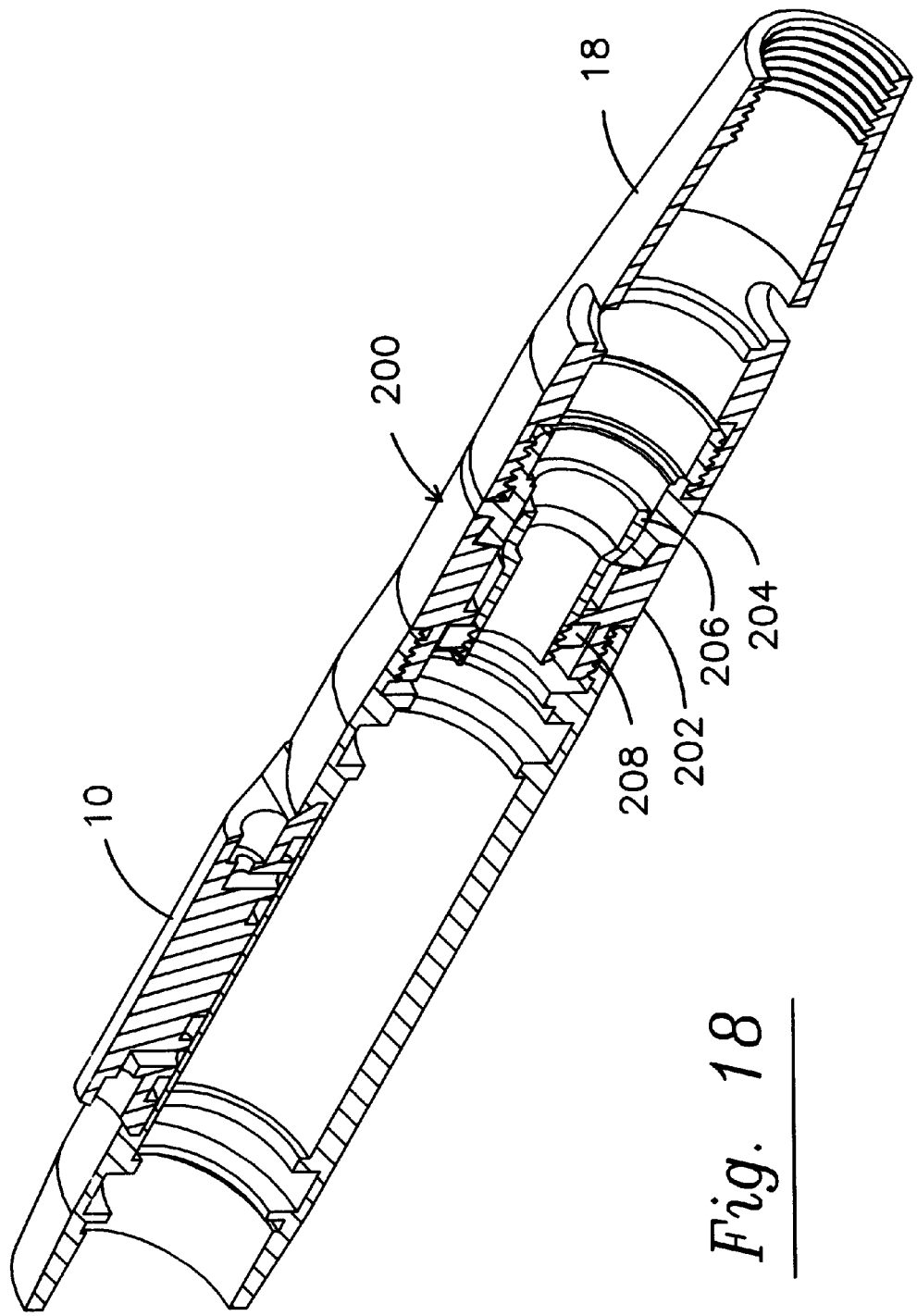
FIG. 18 is a front perspective view in cross-section of an alternate embodiment of a handpiece constructed in accordance with the principles of this invention.
Figure 19:
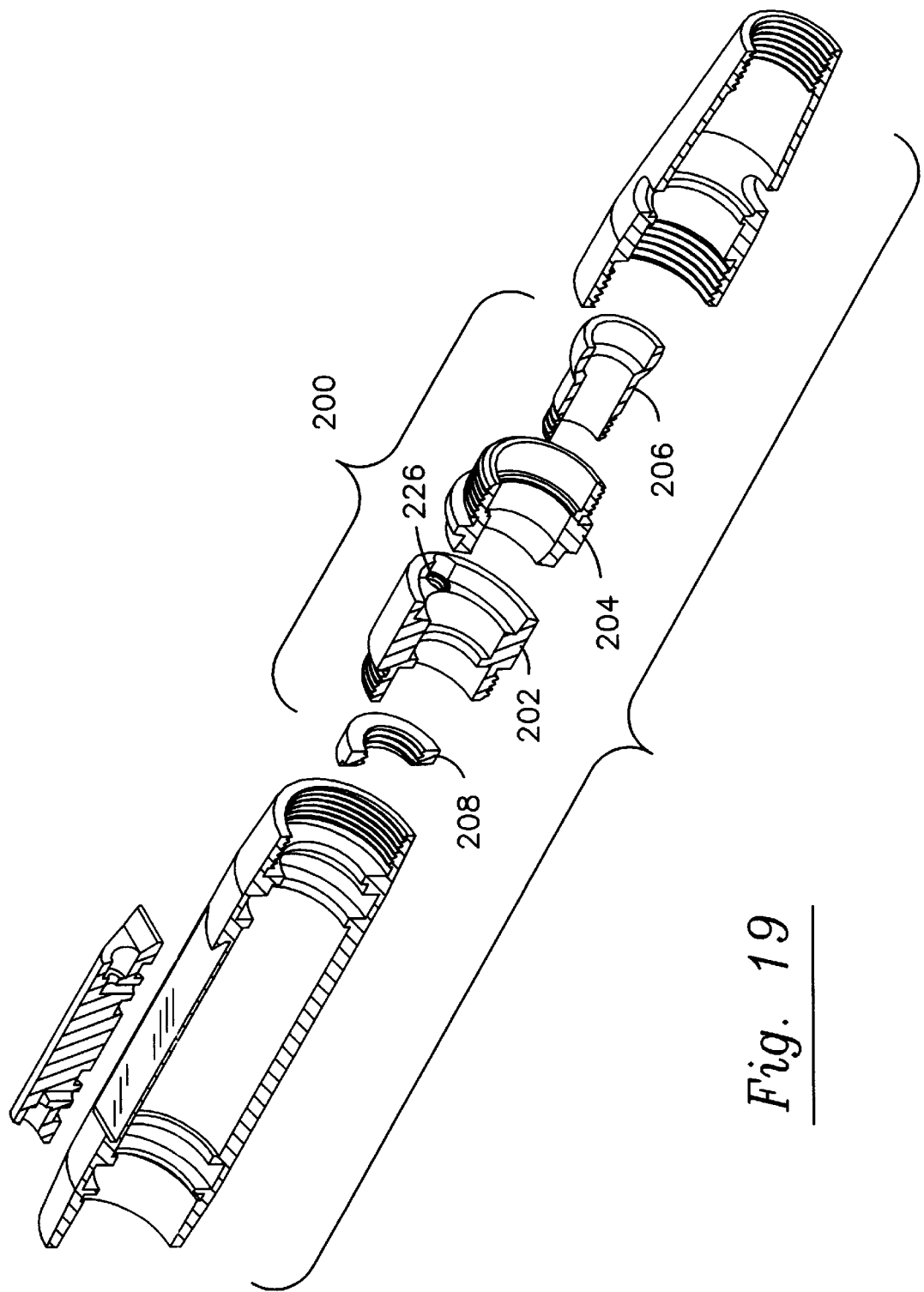
FIG. 19 is an expanded view of FIG. 18.
Figure 20:
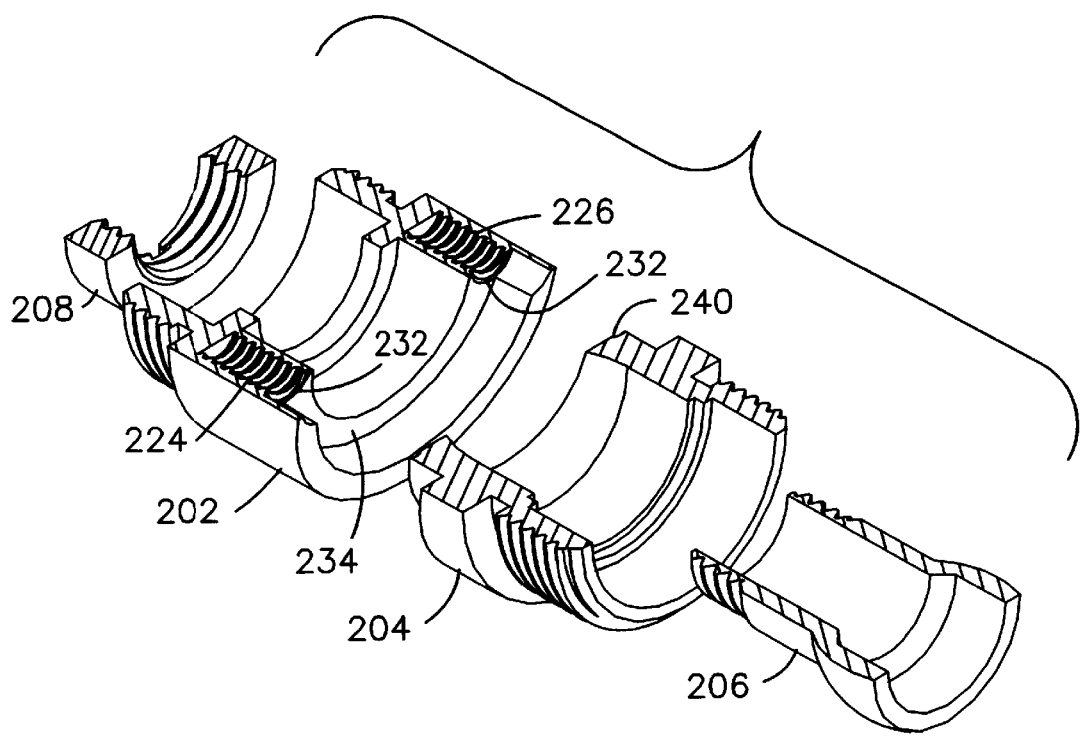
FIG. 20 is an expanded view of the coupling portion of FIG. 19 taken in a plane orthogonal to that of FIG. 19.

As shown in FIGS. 18–20, coupling 200 comprises a stationary sleeve 202, a rotatable indexing sleeve 204 and a cylindrical connecting link 206. FIGS. 19 and 20 are orthogonal views in that FIG. 19 is a cross-section taken through a vertical plane of the handpiece and coupling 200, and FIG. 20 is a cross-section taken through a horizontal plane of the coupling.

Figure 21:
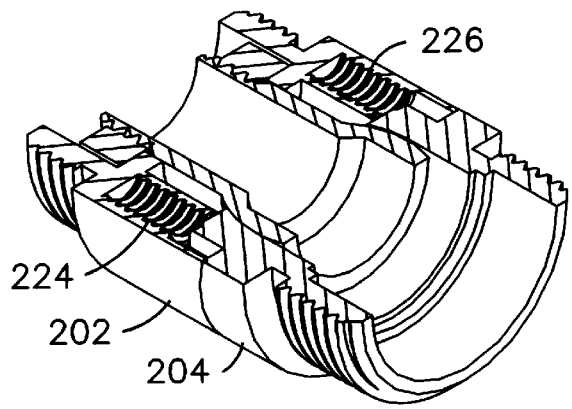
FIG. 21 is an assembled view of FIG. 19 showing the adjustment mechanism in coaxial alignment.
Figure 22:
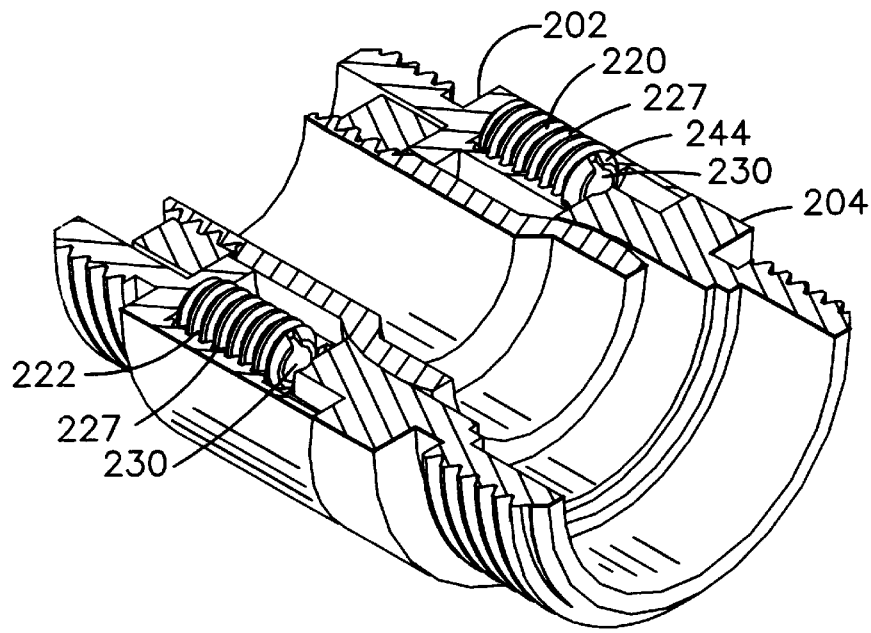
FIG. 22 is a view of FIG. 21 showing the spring assemblies in place.

The outer surfaces of sleeves 202 and 204 are identical to the corresponding outer surfaces of sleeves 30 and 32 of the previous embodiment. Similarly, connecting link 206 and nut 208 threadably attached to its proximal end are also functionally similar to link 40 and nut 50 of the previous embodiment. (However, the axial length of connecting link 206 may be shorter than that of link 40 because of the arrangement of the springs to be discussed below.) While in the previous embodiment the spring biasing the connecting link proximally was an external spring located between stationary sleeve 30 and the outer surface of the connecting link 40, in coupling 200 the bias between stationary sleeve 202 and rotatable sleeve 204 is achieved by an internal spring structure biasing the rotatable sleeve distally. As shown in FIGS. 21 and 22, this internal spring structure comprises engaging elements which, in this embodiment, are a pair of diametrically opposed internal spring assemblies 220 and 222 situated within diametrically opposed chambers 224 and 226 formed in the body of stationary sleeve 202. Spring assemblies 220, 222 each comprise a ball plunger; i.e. an externally threaded cylinder 27 containing a spring 228 and having a ball 230 at its distal end, the spring serving to bias the ball in a distal direction. The spring receiving chambers 224 and 226 are threaded to receive the threaded cylinders of the ball plungers, and each of the threaded cylinders has an opening at its distal end to enable balls 230 to protrude from opening 232 in distally facing surface 234 of stationary sleeve 202. Balls 230 are thus biased against a proximally facing annular surface 240 of stationary sleeve 204.

In the preferred embodiment, each threaded cylinder 227 has a slotted end 244 to facilitate turning the cylinder into its associated chamber. The end 244 is reduced at its distal-most end to provide an aperture 246 in order to retain ball 230 within the insert. It will be understood that each cylinder 227 may be assembled with a spring and ball within its interior prior to being turned or threaded into either chamber 224 or 226.

Figure 23:
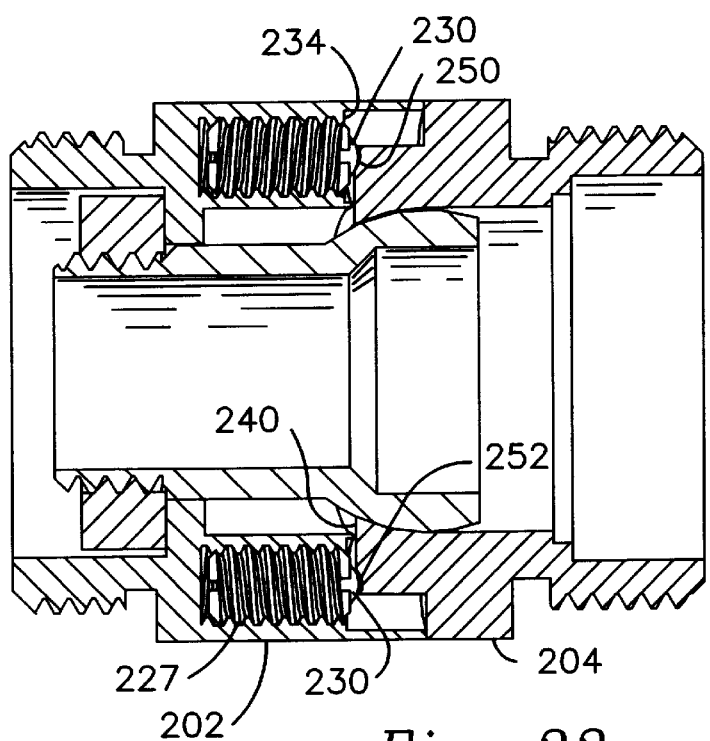
FIG. 23 is a plan view of FIG. 22 wherein the distal end of the coupling is aligned relative to the proximal end.
Figure 24:
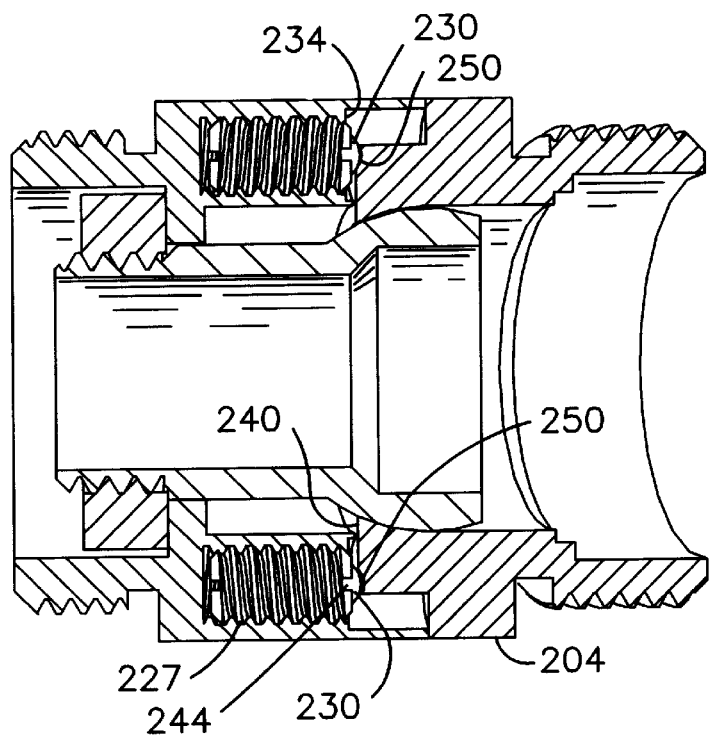
FIG. 24 is a view of FIG. 23 wherein the distal end of the coupling is angled relative to the proximal end.
Figure 25:
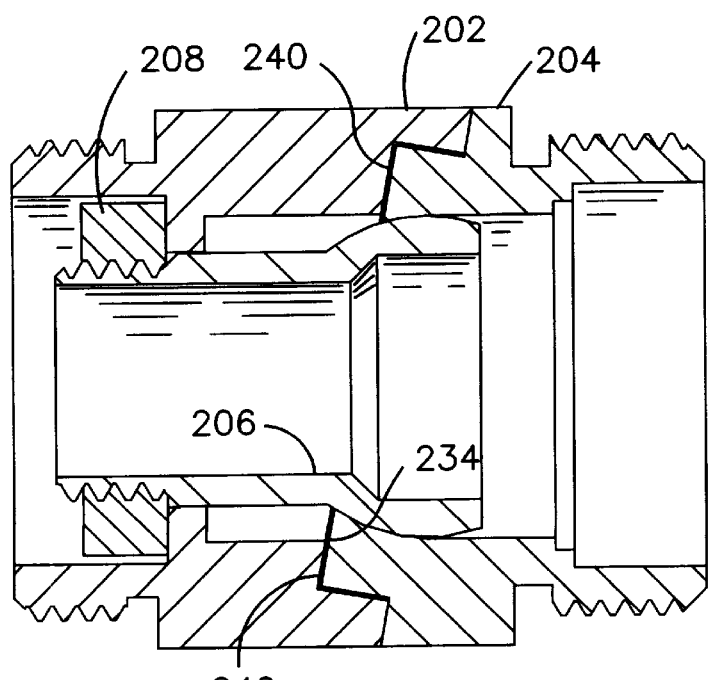
FIG. 25 is a side elevation view of the axially aligned coupling included in FIG. 18, the plane of the drawing being orthogonal to the view shown in FIG. 23.
Figure 26:
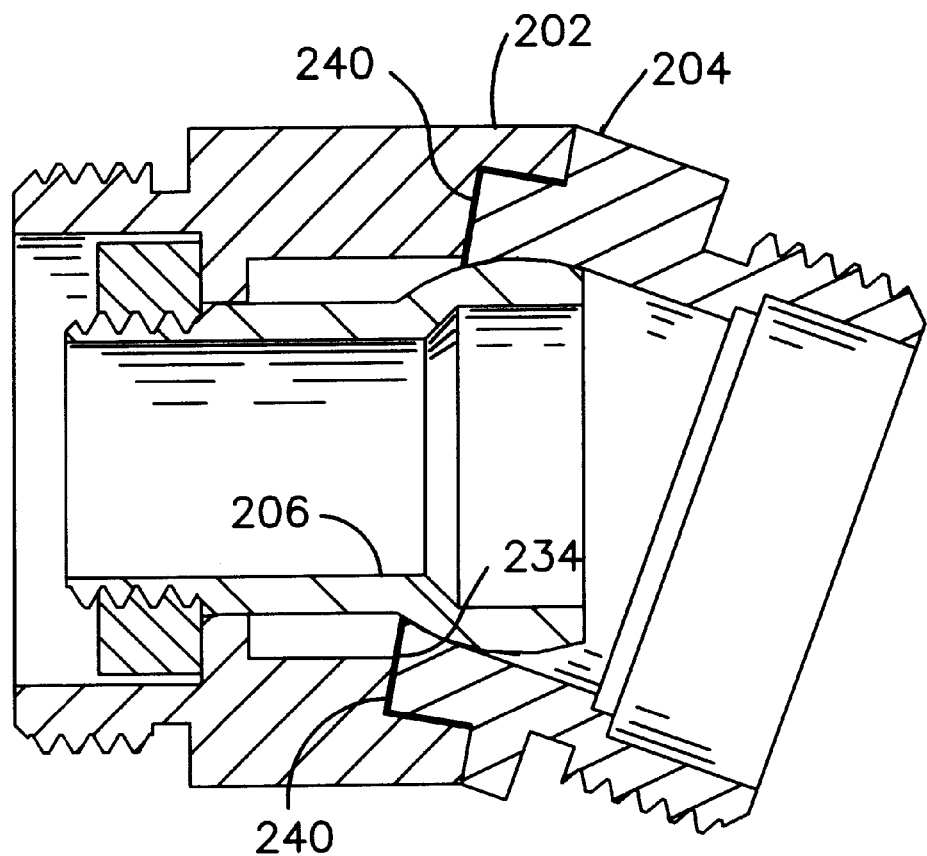
FIG. 26 is a view of FIG. 25 showing the coupling in an angled configuration.

As best seen in FIGS. 23 and 24, balls 230 are biased distally against and received in diametrically opposed recesses 250 and 252 of proximally facing annular surface 240. When the recesses are arranged as shown in FIG. 23, the stationary and rotatable sleeves 202 and 204 are axially aligned as best seen in the elevational view of FIG. 25. The balls and recesses lie within a plane perpendicular to that of FIG. 25 and are not seen in this view. Because annular surfaces 234 and 240 are angled relative to the axis of the sleeves, relative rotation of the sleeves from the position shown in FIGS. 23 and 25 will result in an angled configuration as shown in FIGS. 24 and 26.

It will be understood that coupling 200 does not require a gap such as gap 170 between the tabs used in the previous embodiment. Upon rotating sleeve 204 relative to sleeve 202, the spring loaded balls 230 will be pushed back into spring assemblies 220 and 222 thereby removing the balls from recesses 250 and 252 thereby enabling the sleeves 202 and 204 to be repositioned. This embodiment thus minimizes the likelihood of exposing the interior components of the handpiece and coupling to contaminates in the ambient area. While in the preferred embodiment shown in FIGS. 18–26, a pair of diametrically opposed recesses 250 and 252 are utilized in order to provide the bendable collet mechanism with two selectable positions, it will be understood that one or more additional pairs of diametrically arranged recesses may be added in order to position rotatable indexing sleeve 204 at a variety of selectable angular orientations relative to the handpiece body.

Figure 27:
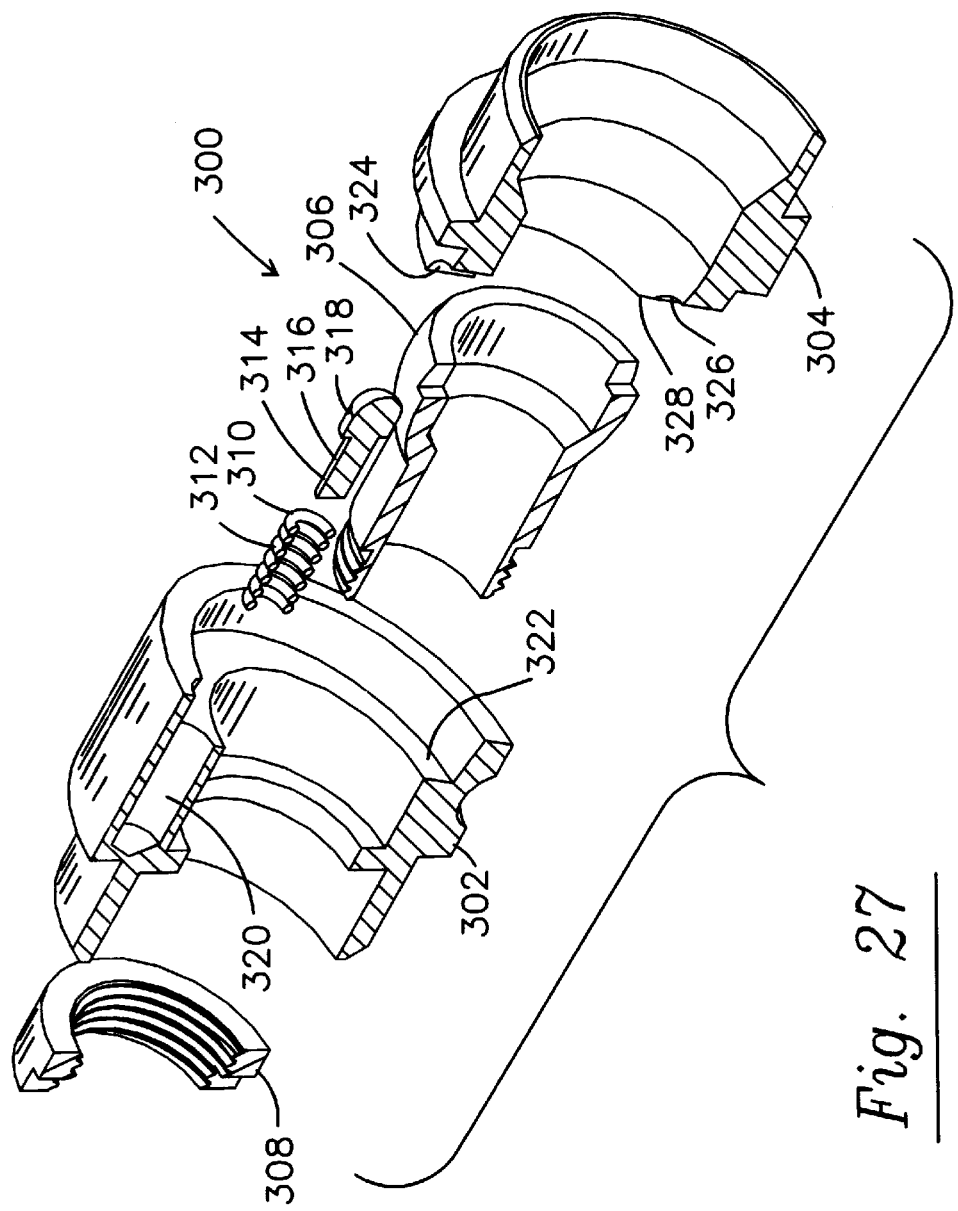
FIG. 27 is an expanded front perspective view, in cross-section, of another alternate embodiment of a handpiece constructed in accordance with the principles of this invention.

A third embodiment of the invention is shown in FIG. 27 as coupling mechanism 300 comprising stationary sleeve 302, a rotatable indexing sleeve 304 and a cylindrical connecting link 306 and associated nut 308. The link 306 and nut 308 operate essentially identically to comparable components in the previously described embodiments. Sleeves 302 and 304 differ from previous embodiments only in that they are adapted to operate with a single internal spring structure 310 biasing the rotatable sleeve 304 distally. Spring structure 310 comprises a coil spring 312 adapted to receive, and bias distally, a locking pin 314 having an elongated body 316 and a distally facing rounded head 318. Spring 312 is received in a chamber 320 formed distally facing surface 322 in stationary sleeve 302 and biases the locking pin distally to seat head 318 in any one of recesses 324, 326 formed in the proximally facing surface 328 of indexing sleeve 304. In the preferred embodiment, the spring structure 310 is situated at the longer side of sleeve 302 in order to enable use of a longer, stronger spring. Coupling 300 operates like the previously described embodiments in that rotation of indexing sleeve 304 serves to orient the sleeve axes as desired.

The invention enables a user to selectively position the tool relative to the handpiece by simply turning the collet mechanism relative to the handpiece and placing it into the detented positions. The resulting orientation of the tool axis relative to the handpiece axis will automatically be maintained without the need to use any other instruments to lock the collet in place. While in the preferred embodiment the angle of the distal axis (of the collet mechanism) may be selectively set at approximately 20° relative to the proximal axis (of the handpiece), it will be understood that other angles may be provided.

It will be understood by those skilled in the art that numerous other modifications and improvements may be made to the preferred embodiments of the invention disclosed herein without departing from the spirit and scope thereof.

What is claimed is:

1. A surgical instrument for driving a tool comprising:
    a handpiece having a proximal end and a distal end, said distal end having a first axis;
    a tool holding means having a proximal end and a distal end, said proximal end having a second axis, said tool holding means for receiving said tool at its distal end; and
    a variable orientation coupling means for orienting said second axis relative to said first axis, said coupling means interposed between and connected to said distal end of said handpiece and said proximal end of said tool holding means, said coupling means selectively movable by a user to situate and maintain said second axis in one of a plurality of positions relative to said first axis; said coupling means further comprising:
    a non-rotatable tubular sleeve having a third axis non-rotatably attached to said distal end of said handpiece, said non-rotatable sleeve having an axial throughbore, a proximal end and a distal end, said distal end having a distally facing annular first surface angularly inclined relative to said third axis by a first predetermined amount;
    a rotatable tubular sleeve having a fourth axis non-rotatably attached to said tool holding means, said rotatable sleeve being rotatable relative to said non-rotatable sleeve, said rotatable sleeve having an axial throughbore, a distal end and a proximal end, said proximal end having a proximally facing annular second surface angularly inclined relative to said fourth axis by a second predetermined amount;
    coupling body means for releasably holding said first and second surfaces together in abutting relation said coupling body means comprising:
    a hollow cylindrical tubular body having a proximal end and a distal end, said tubular body axially aligned within said non-rotatable sleeve; and
    a generally spherical hollow link means secured to and axially aligned at the distal end of said cylindrical tubular body for joining said rotatable and non-rotatable sleeves together, said link means comprising:
    a substantially spherical exterior wall surface secured to said distal end of said hollow tubular body for mating engagement with said rotatable sleeve, and
    a substantially spherical interior wall surface at said proximal end of said rotatable sleeve, said interior wall surface being complementarily shaped spherically to receive said substantially spherical exterior wall surface, said interior wall surface further comprising a proximal-most aperture smaller in size than said exterior wall surface to prevent distal movement of said rotatable sleeve relative to said non-rotatable sleeve.

2. A surgical instrument according to claim 1 wherein said coupling body means comprises:

spring means for urging first and second surfaces and, therefore, said rotatable and non-rotatable sleeves, together.

3. A surgical instrument according to claim 2 further comprising:

detent means for positioning said first and second surfaces in abutting relation in a selected one of a plurality of predetermined positions.

4. A surgical instrument according to claim 2 wherein said spring means is adapted to urge said substantially spherical exterior wall surface proximally.

5. A surgical instrument according to claim 2 wherein said spring means is adapted to urge said substantially spherical interior wall surface distally.

6. A surgical instrument according to claim 5 wherein said spring means further comprises:

at least one engaging element means for being urged by said spring means longitudinally distally, in alignment with the axis of said non-rotatable sleeve, said engaging element means secured to said non-rotatable sleeve;

receiving means fixedly secured to said rotatable sleeve for being engaged by said engaging means to thereby maintain said rotatable sleeve in a selected position relative to said non-rotatable sleeve.

7. A surgical instrument according to claim 6 wherein said at least one engaging element is distally spaced from said distally facing first inclined surface by a predetermined amount.

8. A surgical instrument according to claim 7 wherein said at least one engaging element comprises a rolling ball and wherein said receiving means comprises an annular surface with at least one detent to receive said rolling ball.

9. A surgical instrument according to claim 7 wherein said spring means is a coil spring having an axis longitudinally aligned with said non-rotatable tubular sleeve and further comprising a locking pin comprising an elongated body and a rounded head attached to one end thereof, said elongated body adapted to be received axially within said coil spring so that said rounded head may extend distally therefrom.

10. A surgical instrument according to claim 1 wherein said automatic position holding means comprises:

at least one radially inwardly extending first tab situated adjacent said distal end of said first body of said non-rotatable sleeve, proximally of said distally facing first inclined surface, said first tab extending a first predetermined arcuate distance and aligned parallel to the plane of said distally facing first inclined surface;

at least one radially outwardly extending second tab situated adjacent said proximal end of said second body of said rotatable sleeve, proximally of said proximal facing second inclined surface, said second tab extending a second predetermined arcuate distance and aligned parallel to the plane of said proximally facing second inclined surface, said second tab for selectively engaging the proximal side of said arcuate first tab of said non-rotating sleeve;

a distally facing detent situated on said distally facing first inclined surface of said non-rotatable sleeve; and a proximally facing projection on said proximally facing second inclined surface of said rotatable sleeve whereby, when said non-rotatable and rotatable sleeves are situated in a first position said first and second axes are coaxially aligned when said first and second surfaces are abutting, and when said non-rotatable and rotatable sleeves are situated in a second position said first and second axes are angled relative to each other by a predetermined amount while said first and second surfaces are abutting.

11. A surgical instrument according to claim 10 further comprising at least one pair of said first tabs situated on said non-rotatable sleeve in diametrically opposed relation and at least one pair of said corresponding second tabs in diametrically opposed relation on said rotatable sleeve.

12. A method for selectively positioning a surgical tool into selected positions relative to a powered handpiece for driving the tool, comprising the steps of:

interposing between the handpiece and the tool a variable orientation coupling means which permits nutation of the axis of said tool relative to the axis of said handpiece, said coupling means comprising:

a non-rotatable tubular sleeve having an axis non-rotatably attached to said handpiece, said non-rotatable sleeve having a proximal end and a distal end, said distal end having a distally facing first surface angularly inclined relative to said axis of said non-rotatable sleeve by a first predetermined amount;

a rotatable tubular sleeve having an axis non-rotatably attached to said tool holding means, said rotatable sleeve being rotatable relative to said non-rotatable sleeve, said rotatable sleeve having a distal end and a proximal end, said proximal end having a proximally facing second surface angularly inclined relative to said axis of said rotatable sleeve by a second predetermined amount;

coupling body means for releasably holding said first and second surfaces together in abutting relation;

selectively positioning said non-rotatable sleeve at a predetermined position relative to said second body; and using a spring to provide tension between said first and second surfaces.

13. In a surgical instrument comprising a handpiece having a first axis, a tool holding means having a second axis and a variable orientation coupling means for orienting said second axis relative to said first axis, said coupling means interposed between and connected to said handpiece and said tool holding means, said coupling means comprising a first body having a third axis, attached to said distal end of said handpiece and having a distally facing first surface angularly inclined relative to said third axis by a first predetermined amount, a second body having a fourth axis, attached to said tool holding means and having a proximally facing second surface angularly inclined relative to said fourth axis by a second predetermined amount; and coupling body means for holding said first and second surfaces together in abutting relation, the improvement wherein said coupling body means comprises:

a hollow cylindrical tubular body having a proximal end and a distal end, said tubular body axially aligned within said first body;

a generally spherical hollow link means secured to and axially aligned at the distal end of said cylindrical tubular body for joining said first and second bodies together, said link means comprising:

a substantially spherical exterior wall surface secured to said distal end of said hollow tubular body for mating engagement with said second body, and a substantially spherical interior wall surface of said proximal end of said second body, said interior wall surface being complementarily shaped spherically to receive said substantially spherical exterior wall surface, said interior wall surface further comprising a proximal-most aperture smaller in size than said exterior wall surface to prevent distal movement of said second body relative to said first body.

14. In a surgical instrument comprising a handpiece having a first axis, a tool holding means having a second axis and a variable orientation coupling means for orienting said second axis relative to said first axis, said coupling means interposed between and connected to said handpiece and said tool holding means, said coupling means comprising a first body having a third axis, attached to said distal end of said handpiece and having a distally facing first surface angularly inclined relative to said third axis by a first predetermined amount, a second body having a fourth axis, attached to said tool holding means and having a proximally facing second surface angularly inclined relative to said fourth axis by a second predetermined amount; and coupling body means for holding said first and second surfaces together in abutting relation, an automatic position holding means comprising:

at least one radially inwardly extending first tab situated adjacent said distal end of said first body, proximally of said distally facing first inclined surface, said first tab extending a first predetermined arcuate distance and aligned parallel to the plane of said distally facing first inclined surface;

at least one radially outwardly extending second tab situated adjacent said proximal end of said second body, proximally of said proximal facing second inclined surface, said second tab extending a second predetermined arcuate distance and aligned parallel to the plane of said proximally facing second inclined surface, said second tab for selectively engaging the proximal side of said arcuate first tab of said first body;

a distally facing detent situated on said distally facing first inclined surface of said first body; and a proximally facing projection on said proximally facing second inclined surface of said second body whereby, when said first and second bodies are situated in a first position said first and second axes are coaxially aligned when said first and second surfaces are abutting, and when said first and second bodies are situated in a second position said first and second axes are angled relative to each other by a predetermined amount while said first and second surfaces are abutting.

* * * * *